United States Patent

Cohen et al.

[11] Patent Number: 5,457,124
[45] Date of Patent: Oct. 10, 1995

[54] CARBOXYLIC ACID LEUKOTRIENE B4 ANTAGONISTS

[75] Inventors: Noal Cohen, Montclair; Andrzej R. Daniewski, Nutley; Ferdinand K. Lee, Teaneck; Keith A. Yagaloff, Hohokus, all of N.J.

[73] Assignee: Hoffmann-La Roche Inc., Nutley, N.J.

[21] Appl. No.: 164,116

[22] Filed: Dec. 7, 1993

[51] Int. Cl.$^6$ .................. A61K 31/35; C07D 311/76
[52] U.S. Cl. .................. 514/456; 514/513; 514/543; 562/462; 560/53; 560/54; 549/401
[58] Field of Search .................. 549/401; 560/53, 560/54; 562/462; 514/456, 513, 543

[56] References Cited

U.S. PATENT DOCUMENTS

| | | | |
|---|---|---|---|
| 4,281,008 | 7/1981 | Chamberlain et al. | 549/401 |
| 4,499,299 | 2/1985 | Bernstein et al. | 560/53 |
| 4,546,194 | 10/1985 | Miyano et al. | 549/401 |
| 4,565,882 | 1/1986 | Miyano et al. | 549/401 |
| 4,665,203 | 5/1987 | Miyano et al. | 549/401 |
| 4,683,325 | 7/1987 | Frenette et al. | 562/462 |
| 4,686,235 | 8/1987 | Chang et al. | 560/53 |
| 4,841,076 | 6/1989 | Kitagawa et al. | 549/401 |
| 4,889,871 | 12/1989 | Djuric et al. | 514/456 |
| 4,935,529 | 6/1990 | Yerwick | 549/401 |
| 4,950,684 | 8/1990 | Koszyk et al. | 514/456 |
| 4,952,705 | 8/1990 | Miyano et al. | 549/401 |
| 5,219,883 | 6/1993 | Koszyk et al. | 514/456 |
| 5,273,999 | 12/1993 | Cohen et al. | 514/456 |
| 5,310,952 | 5/1994 | Heveling et al. | 549/401 |

*Primary Examiner*—C. Warren Ivy
*Assistant Examiner*—A. A. Owens
*Attorney, Agent, or Firm*—George M. Gould; George W. Johnston; Robert A. Silverman

[57] ABSTRACT

The invention relates to compounds selected from the group consisting of the formulas:

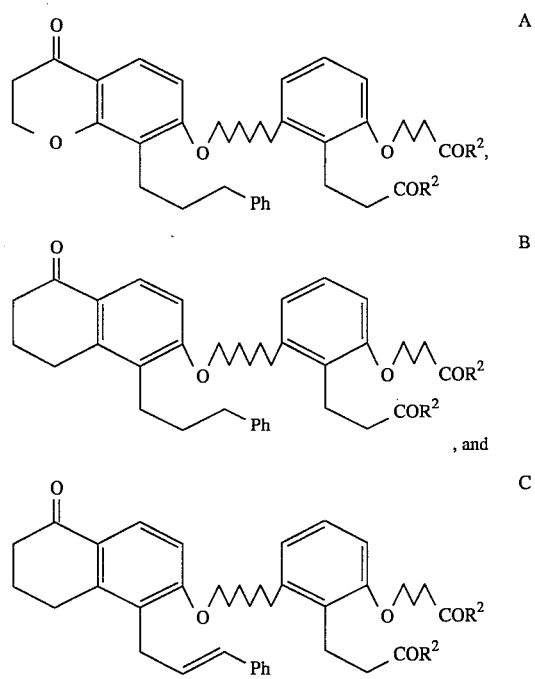

wherein $R^2$ and Ph are as described herein. These compounds are potent leukotriene $B_4$ antagonists and are therefore useful in the treatment of inflammatory diseases.

20 Claims, No Drawings

CARBOXYLIC ACID LEUKOTRIENE B4 ANTAGONISTS

BRIEF DESCRIPTION OF THE INVENTION

The invention relates to a compound selected from the group consisting of compounds of the formulas

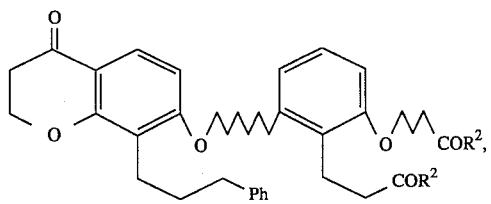

A

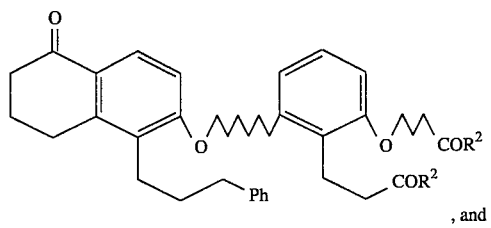

B

, and

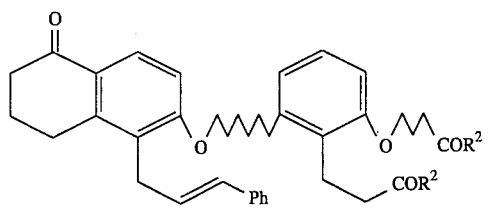

C wherein $R^2$, each occurrence independently, is hydroxy, lower alkoxy or $NR^3R^4$, wherein $R^3$ and $R^4$, independently, are hydrogen or lower alkyl, and Ph is phenyl and, for the compound of formula C, its geometric isomer, and, when $R^2$ is hydroxy, a pharmaceutically acceptable salt thereof with a base.

The compounds of formula A, B and C are potent leukotriene $B_4$ antagonists and are therefore useful in the treatment of inflammatory diseases such as psoriasis, rhinitis, chronic obstructive pulmonary disease, inflammatory bowel disease, asthma, acute respiratory distress syndrome, cystic fibrosis, allergy, arthritis such as rheumatoid arthritis, dermatitis such as contact dermatitis, NSAID-induced gastropathy, gout, ischemia/reperfusion injury, and trauma induced inflammation, such as spinal cord injury.

In another aspect, the invention relates to pharmaceutical compositions and methods of use comprising the compounds of formulas A, B and C.

In yet another aspect, the invention relates to an intermediate 2-(3-phenylpropenylidene)-1,3-cyclohexanedione, which is of the formula:

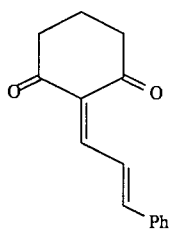

V-3 wherein Ph is phenyl and to an intermediate 3-(2-cyanoethoxy)-2-(3-phenylpropyl)-2-cyclohexen-1-one, which is of the formula:

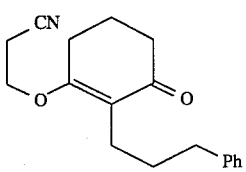

V-6 wherein Ph is phenyl.

DETAILED DESCRIPTION OF THE INVENTION

The invention relates to a compound selected from the group consisting of compounds of the formulas

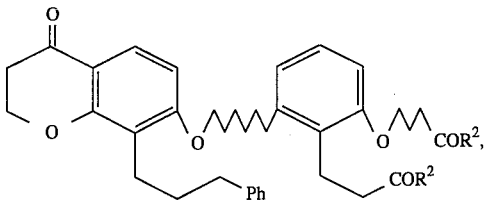

A

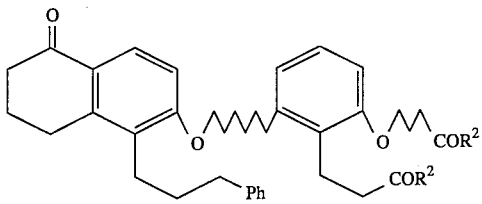

B

, and

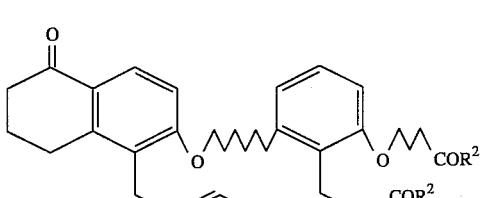

C wherein $R^2$, each occurrence, independently, is hydroxy, lower alkoxy or $NR^3R^4$, wherein $R^3$ and $R^4$, independently, are hydrogen or lower alkyl, and Ph is phenyl and, for the compound of formula C, its geometric isomer, and, when $R^2$ is hydroxy, a pharmaceutically acceptable salt thereof with a base.

As used herein, the term "lower alkyl" denotes a straight or branched chain saturated hydrocarbon containing 1 to 7 carbon atoms, preferably from 1 to 4 carbon atoms, for example, methyl, ethyl, propyl, isopropyl, butyl, t-butyl, neopentyl, pentyl, heptyl, and the like. The term "lower alkoxy" denotes an alkyl ether group in which the alkyl group is as described above, for example, methoxy, ethoxy, propoxy, pentoxy and the like.

As used herein, a leaving group denotes halogen, preferably, bromine and iodine; lower alkylsulfonyloxy, such as, (methylsulfonyl)oxy, (trifluoromethylsulfonyl)oxy or the like; (arylsulfonyl)oxy, such as, (para-toluenesulfonyl)oxy or the like.

2-(3-Carboxypropoxy)-6-[6-[[3,4-dihydro-4-oxo-8-(3-phenylpropyl)-2H- 1-benzopyran-7-yl]oxy]hexyl]benzenepropanoic acid (a compound of formula A);

2-(3-Carboxypropoxy)-6-[6-[[5,6,7,8 -tetrahydro-5-oxo-1-(3-phenylpropyl)-2-naphthalenyl] oxy]hexyl]benzenepropanoic acid (a compound of formula B ); and (E)-2-(3-Carboxypropoxy)-6-[6-[[5,6,7,8-tetrahydro-5-oxo-1-(3-phenyl-2 -propenyl)-2-naphthaleny]oxy]hexyl]benzenepropanoic acid (a compound of formula C).

The Compounds of formulas A, B and C can be prepared as hereinafter described in Reaction Schemes I–VI.

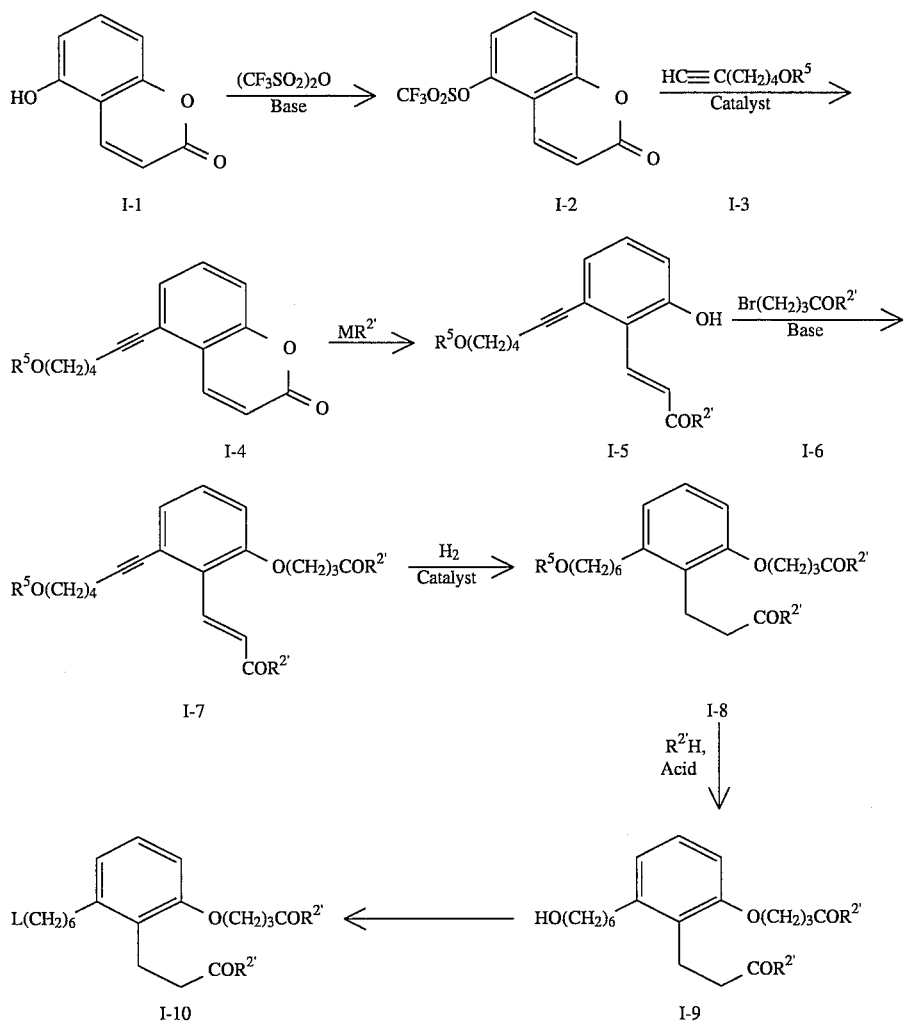

Reaction Scheme I

As used herein, an acid sensitive hydroxyl protecting group denotes, preferably, tetrahydropyranyl, 1-ethoxyethyl, 1-methyl-1-methoxyethyl and the like.

As used herein, an alkali metal denotes, preferably, lithium, sodium, potassium, and cesium.

As used herein, a hydroxyl protecting group removable by hydrogenolysis denotes, preferably, benzyl, p-methoxybenzyl, triphenylmethyl, and the like.

A preferred group of compounds is represented by formulas A, B, and C.

Most preferred examples of this invention are:

wherein $R^{2'}$ is lower alkoxy, $R^5$ is an acid sensitive hydroxyl protecting group, L is a leaving group, and M is an alkali metal.

In Reaction Scheme I, 5-hydroxycoumarin, a known compound of formula I-1 is converted to the corresponding trifluoromethanesulfonic ester I-2 by treatment with trifluoromethanesulfonic anhydride in the presence of an amine base. Any conventional amine base may be utilized. Pyridine or triethylamine are preferred. This transformation is preferably carried out in dichloromethane solvent at a temperature in the range of 0°–25° C. The compound of formula I-2 can be recovered by conventional means such as chromatography or recrystallization.

The compound of formula I-2 is allowed to react with an acetylenic compound of formula I-3, which represents known compounds, in the presence of a palladium catalyst and an amine base giving the compound of formula I-4. It is preferred that this transformation be carried out using dichlorobis(triphenylphosphine)palladium(II) as the catalyst and triethylamine as the base, in dimethylformamide solvent, at a temperature in the range of 80°–100° C. The product of formula I-4 is recovered using conventional chromatographic techniques.

The compound of formula I-4 is converted to the corresponding hydroxy cinnamate of formula I-5 by alcoholysis of the lactone ring using an alkali metal lower alkoxide in a lower alkanol solvent. This transformation is carried out using lithium, sodium, or potassium lower alkoxide. It is preferred that this transformation be carried out in methanol or ethanol with sodium methoxide or sodium ethoxide, at a temperature in the range of 60°–80° C. The compound of formula I-5 is recovered by standard chromatographic methods or by recrystallization.

Alkylation of the compound of formula I-5 with the bromo ester of formula I-6, which represents known compounds, is carried out in the presence of a base, for example, an alkali metal carbonate such as sodium or potassium carbonate, at a temperature in the range of from about 25° C. to about 110° C., in a polar, aprotic solvent such as acetonitrile, N,N-dimethylformamide, 2-butanone, dimethyl sulfoxide and the like, and affords the compound of formula I-7 which is recovered by chromatography.

Catalytic hydrogenation of the compound of formula I-7 gives the corresponding saturated compound of formula I-8. This hydrogenation is carried out under conventional conditions. More specifically, a supported transition metal catalyst, such as 5% or 10% palladium metal on carbon is preferred. It is also preferred that the hydrogenation be carried out at ambient temperature and under one atmosphere of hydrogen gas pressure.

Preferred solvents for the hydrogenation are lower alkanols such as methanol or ethanol, or ester solvents such as ethyl acetate, or the like. Mixtures of these solvents can also be used.

Removal of the protecting group $R^5$ in the compound of formula I-8 to give the corresponding alcohol of formula I-9 is carried out using an acidic catalyst. It is preferred that this deprotection process be carried out in a lower alkanol solvent such as methanol or ethanol. Useful acid catalysts for effecting this deprotection are organic sulfonic acids or amine salts thereof, at a temperature within the range of 20°–80° C. It is particularly preferred that this transformation be carried out using para-toluenesulfonic acid in methanol. The compound of formula I-9 is recovered by conventional chromatography.

The compound of formula I-9 is converted to the corresponding derivative I-10 using standard methods known in the art for transforming hydroxy groups into leaving groups. These methods include treatment with halogenating reagents such as N-bromosuccinimide/triphenylphosphine or N-chlorosuccinimide/triphenylphosphine in dichloromethane. Alternatively, the compound of formula I-9 can be converted to the corresponding sulfonic ester of formula I-10 by conventional methods such as treatment with an alkyl- or arylsulfonyl chloride and an organic amine. It is preferred that the compound of formula I-9 be treated with methanesulfonyl chloride and triethylamine in dichloromethane, ether, or ethyl acetate, at a temperature in the range of 0°–25° C. These methanesulfonic esters can in turn be converted into the corresponding iodides of formula I-10 by treatment with an alkali metal iodide in a polar, aprotic solvent. It is preferred that this conversion be carried out using sodium iodide, in acetonitrile, within a temperature range of 20°–80° C. The compounds of formula I-10 are recovered by conventional extractive work-up.

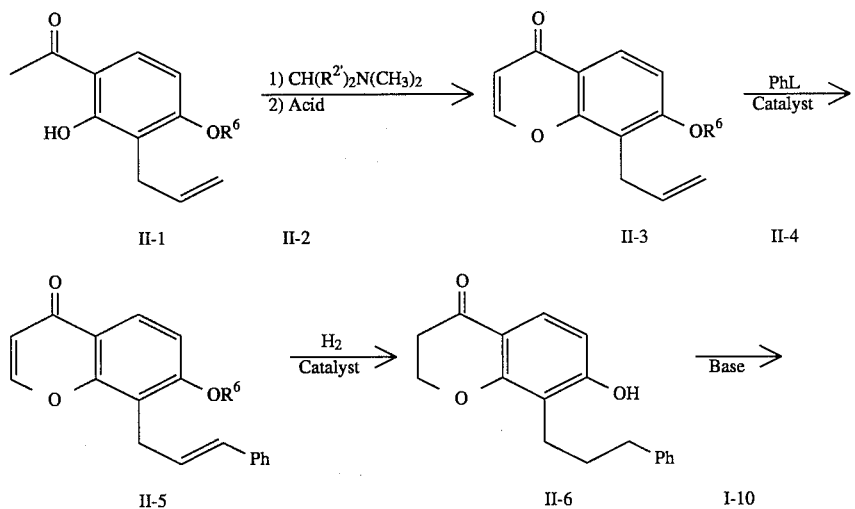

Reaction Scheme II

-continued
Reaction Scheme II

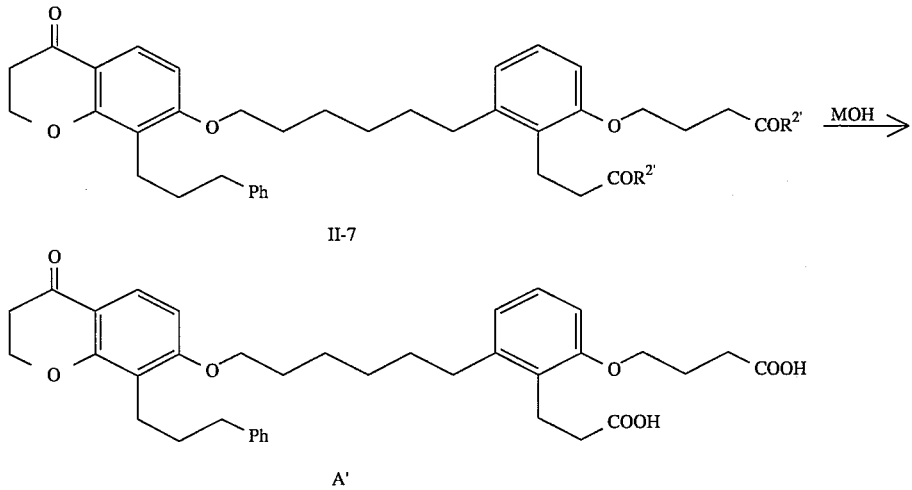

wherein $R^6$ is an hydroxyl protecting group removable by hydrogenolysis and $R^{2'}$, L, and M are as previously described.

In Reaction Scheme II, an ortho-hydroxyacetophenone of formula II-1, which represents known compounds, is treated with a known formamide acetal of formula II-2, at temperatures in the range of from 120° C. to 160° C., in an aromatic hydrocarbon solvent, preferably xylene, to give an intermediate which is not purified, but immediately cyclized by acid treatment to the chromone product II-3. Preferred acids for effecting this cyclization include the organic sulfonic acids such as para-toluenesulfonic acid. Preferred solvents for carrying out this cyclization include the lower alkanols such as methanol and ethanol, at temperatures in the range of 60° C. to 80° C. The chromone of formula II-3 is recovered by conventional chromatographic methods or by recrystallization.

The chromone of formula II-3 is condensed with a benzene derivative of formula II-4, which represents known compounds, in the presence of a base, a palladium catalyst, and a quaternary ammonium salt, to give a product of formula II-5. Exemplary of the benzene derivative are known compounds such as iodobenzene, phenyl trifluoromethanesulfonate, and the like. It is preferred that this condensation be carried out using an alkali metal acetate as the base and a tetraalkyl-ammonium halide salt as the quaternary ammonium salt. It is especially preferred that the base be sodium acetate and the quaternary ammonium salt be tetraethylammonium chloride. In this condensation, the preferred catalyst is palladium(II) acetate. This condensation is preferably carried out within a temperature range of 25°–100° C., in a polar, aprotic solvent such as N,N-dimethylformamide. The compound of formula II-5 is recovered by conventional chromatography or recrystallization.

Catalytic hydrogenation of the chromone of formula II-5, with concomitant hydrogenolytic cleavage of the protecting group $R^6$ gives the hydroxy chromanone of formula II-6. This hydrogenation is carried out under conventional conditions. A supported transition metal catalyst is preferred such as 5% or 10% palladium metal on carbon or charcoal. It is preferred that this hydrogenation be carried out at ambient temperature and under one atmosphere of hydrogen gas pressure. Preferred solvents for effecting is hydrogenation are the lower alkanols such as methanol or ethanol, or ester solvents such as ethyl acetate. Mixtures of these solvents can also be used. This hydrogenation can be carried out in two stages, first removing the protecting group with palladium on carbon and then reducing the double bonds using conventional Raney nickel catalyst. The compound of formula II-6 can be isolated by conventional chromatographic means or by recrystallization.

The hydroxy chromanone of formula II-6 is allowed to react with a compound of formula I-10 (Reaction Scheme I) in the presence of a base, for example, an alkali metal carbonate such as sodium or potassium carbonate, at a temperature in the range of from about 25° C. to about 110° C., in a polar, aprotic solvent such as acetonitrile, N,N-dimethylformamide, 2-butanone, dimethyl sulfoxide and the like. An alkali metal hydride such as sodium hydride can also be used as the base in which case an inert solvent such as tetrahydrofuran, ether, toluene, or N,N-dimethylformamide is preferred. Alternatively, the procedure of U.S. Pat. No. 4,931,574 can be utilized. In this variation, compounds of formulas II-6 and I-10 are allowed to react in the presence of an alkali metal carbonate, preferably potassium carbonate, and a phase transfer catalyst preferably tris[2-(2-methoxyethoxy)ethyl]amine (TDA-1 ), in an aromatic hydrocarbon solvent, preferably toluene, at a temperature in the range of 80° C. to 110° C. The resulting diester of formula II-7 can be recovered utilizing conventional methods such as chromatography, and can be converted by saponification using an alkali metal hydroxide such as lithium, sodium, or potassium hydroxide, in a solvent mixture of water and a water miscible solvent such as methanol, ethanol, or tetrahydrofuran, at a temperature in the range of from about 25° C. to about 60° C., to the corresponding diacid of formula A'. It is preferred that this saponification be carried out using lithium hydroxide, in aqueous tetrahydrofuran, at ambient temperature. The compounds of formula A' can be recovered by conventional methods such as recrystallization or chromatography.

Reaction Scheme III

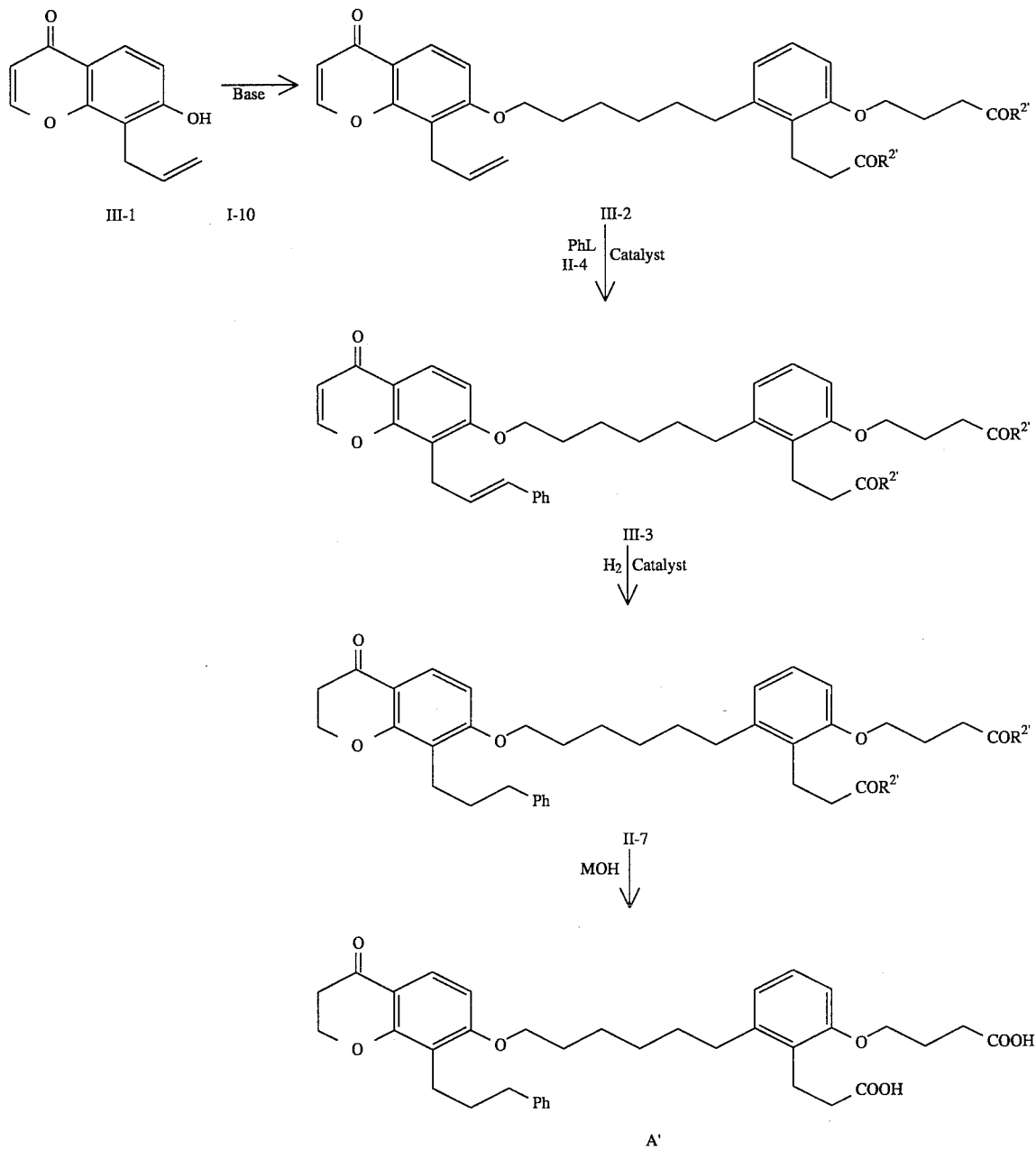

wherein L, M and R$^{2'}$ are as previously described.

In Reaction Scheme III, the known hydroxy chromone of formula III-1 is alkylated with the compound of formula I-10 as described in Reaction Scheme II for the conversion of the compound of formula II-6 to the compound of formula II-7. The product of formula III-2 is recovered by conventional chromatography and is phenylated to give the compound of formula III-3 as described in Reaction Scheme II for the conversion of the compound of formula II-3 to the compound of formula II-5. The compound of formula III-3 is recovered by conventional chromatography. Catalytic hydrogenation of the compound of formula III-3 gives the corresponding compound of formula II-7 which is recovered by chromatography. This hydrogenation is carried out under conditions described in Reaction Scheme II for the conversion of the compound of formula II-5 to the compound of formula II-6. Saponification of the compound of formula II-7 affords the corresponding diacid of formula A' as described in Reaction Scheme II.

Reaction Scheme IV

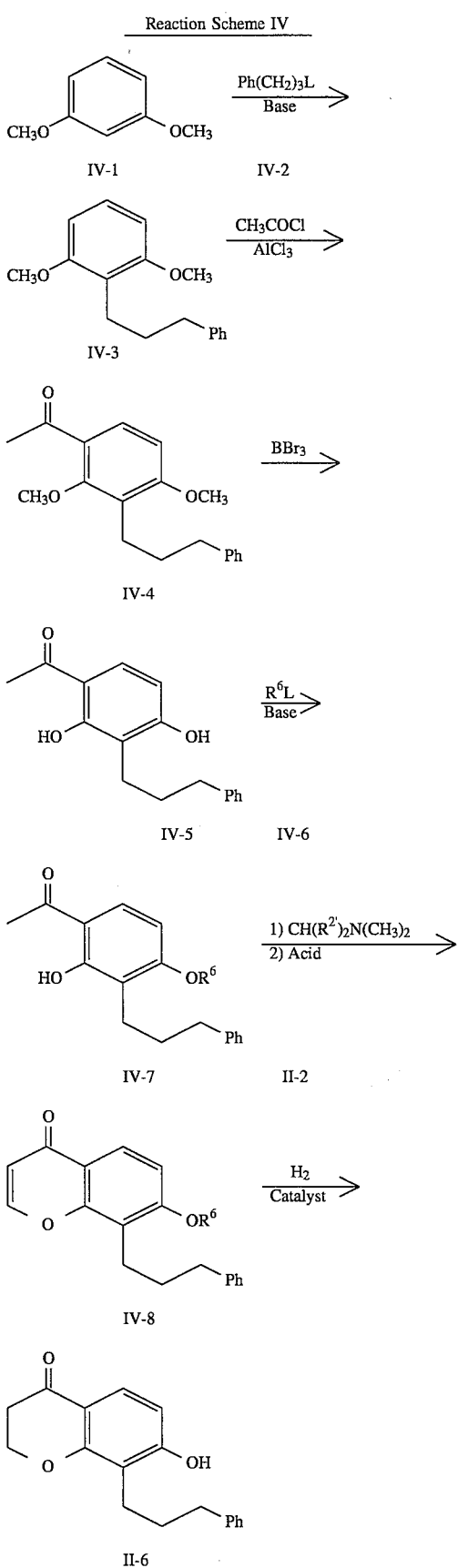

wherein $R^{2'}$, $R^6$, and L are as previously described.

In Reaction Scheme IV, 1,3-dimethoxybenzene, a known compound of formula IV-1, is converted into the product of formula IV-3 by first treatment with a strong base followed by the alkylating agent of formula IV-2 which represents known compounds such as 3-bromo-1-phenylpropane, 3-iodo-1-phenylpropane, 3-[(methylsulfonyl)oxy]-1-phenylpropane, and the like. It is preferred that the base used in this alkylation be an organolithium species such as methyllithium, phenyllithium, n-butyllithium and the like and that the alkylation be carried out in an inert ether solvent. It is particularly preferred that the alkylation be carried out using n-butyllithium in tetrahydrofuran, at a temperature of from −20° C. to room temperature. The product of formula IV-3 is recovered by conventional chromatography.

Acetylation of the compound of formula IV-3 is carried out under standard Friedel-Crafts conditions, specifically treatment with acetyl chloride and aluminum chloride, in dichloromethane, giving the corresponding acetophenone product of formula IV-4 which is recovered by chromatography. Treatment of the compound of formula IV-4 under standard demethylation conditions, such as using boron tribromide in dichloromethane solution, at from −50° C. to room temperature, gives the corresponding dihydroxy-acetophenone product of formula IV-5 which is recovered by conventional chromatography or recrystallization.

The dihydroxyacetophenone of formula IV-5 is allowed to react with a compound of formula IV-6, which represents known compounds, in the presence of a base, giving the compound of formula IV-7. Among the various compounds of formula IV-6 which can be employed, benzyl chloride or benzyl bromide are preferred. It is preferred that this alkylation be carried out using potassium carbonate as the base, in acetone or acetonitrile, within a temperature range of 20°–80° C. Treatment of the compound of formula IV-7 with a known formamide acetal of formula II-2 followed by acidic cyclization, as described in Reaction Scheme II for the conversion of the compound of formula II-1 to the compound of formula II-3, gives the chromone product IV-8. This chromone IV-8 is generally recovered by conventional chromatographic methods or by recrystallization. Catalytic hydrogenation of the chromone IV-8, with concomitant hydrogenolytic cleavage of the arylmethyl ether moiety $R^6$ gives the chromanone of formula II-6. This hydrogenation-hydrogenolysis is carried out as described in Reaction Scheme II for the conversion of the compound of formula II-5 to chromanone II-6.

Reaction Scheme V

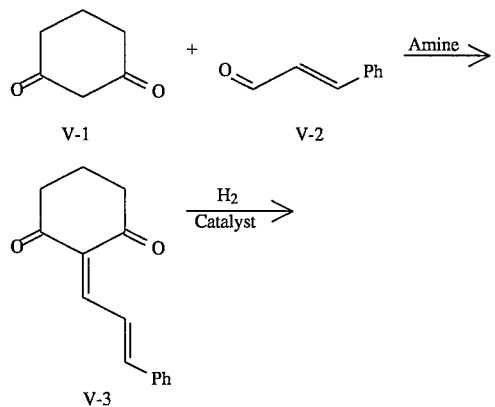

-continued
Reaction Scheme V

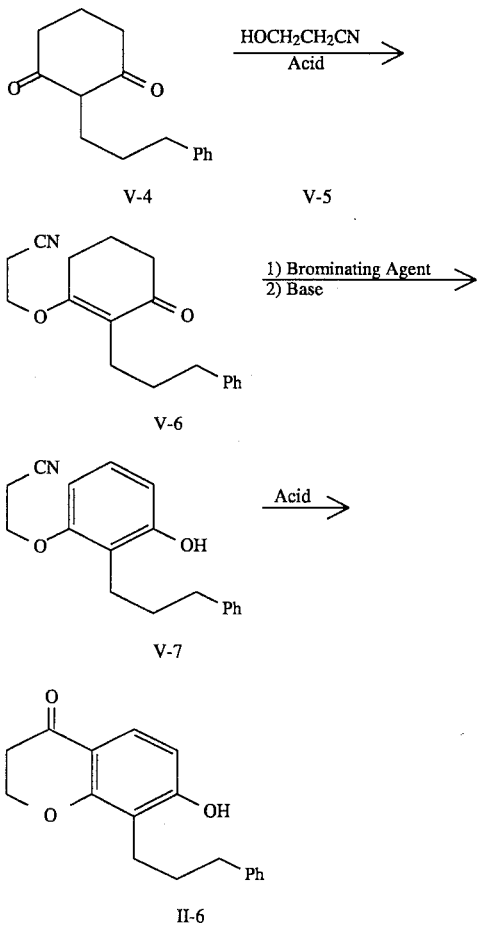

In Reaction Scheme V, 1,3-cyclohexanedione, a known compound of formula V-1 is condensed with the known compound, cinnamaldehyde, of formula V-2, in the presence of a secondary amine catalyst, to give the diene dione product of formula V-3 which is recovered by crystallization. It is preferred that this aldol condensation be carried out using a cyclic secondary amine, specifically, piperidine as the catalyst, in ethanol solvent, within a temperature range of from 0° to 30° C.

Catalytic hydrogenation of the diene dione of formula V-3 is carried out using palladium on carbon as the catalyst in ethyl acetate solution, to give the corresponding cyclohexanedione product of formula V-4. It is preferred that this hydrogenation be carried out at ambient temperature and under one atmosphere of hydrogen gas pressure.

The compound of formula V-4 is treated with the known compound, 3-hydroxy-propionitrile of formula V-5, in the presence of an acid catalyst, to afford the the enol ether product of formula V-6 which is recovered by conventional chromatography. It is preferred that this reaction be carried out using an organic sulfonic acid such as paratoluenesulfonic acid as the catalyst in an inert hydrocarbon solvent such as benzene or toluene, within a temperature range of from 80° to 120° C.

Aromatization of the enol ether of formula V-6 to give the corresponding phenol of formula V-7 is achieved by bromination followed by dehydrobromination with a base. The bromination can be effected with any of the common brominating reagents such as bromine, N-bromosuccinimide, and the like, in an inert solvent. It is preferred that this bromination be carried out using 1,3-dibromo-5,5-dimethylhydantoin, in dichloromethane solution, within a temperature range of from −10° to 5° C. The dehydrobromination can be effected using a sterically hindered tertiary amine base, in an inert solvent. It is preferred that the dehydrobromination be carried out using 1,4-diazabicyclo[2.2.2]octane as the base, in toluene solution, within a temperature range of from 25° to 110° C. The phenol of formula V-7 is recovered by chromatography.

Cyclization of the phenol of formula V-7 is carried out by treatment with strong acid to give the hydroxy chromanone of formula II-6 which is recovered by chromatography or crystallization. This cyclization can be achieved using conventional strong acids such as sulfuric acid, hydrochloric acid, phosphoric acid and the like. It is preferred that this cyclization be carried out using 85% phosphoric acid, in acetic acid solution, within a temperature range of from 100° to 150° C.

Reaction Scheme VI

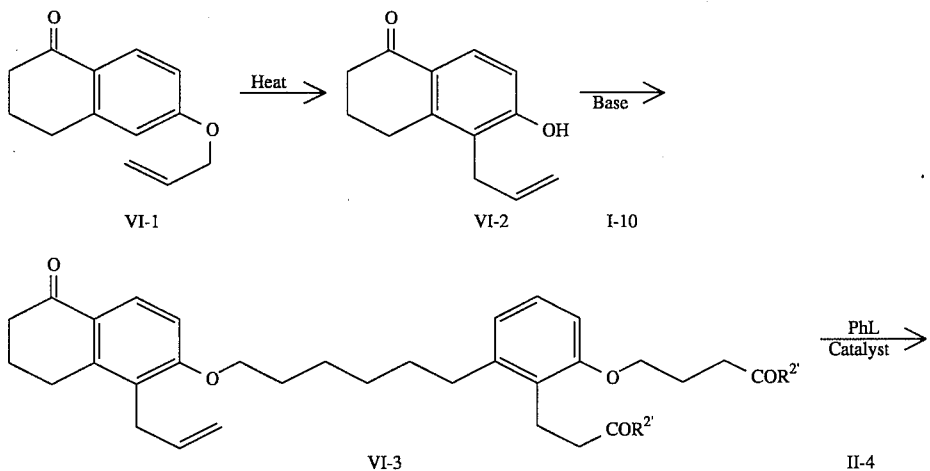

-continued
Reaction Scheme VI

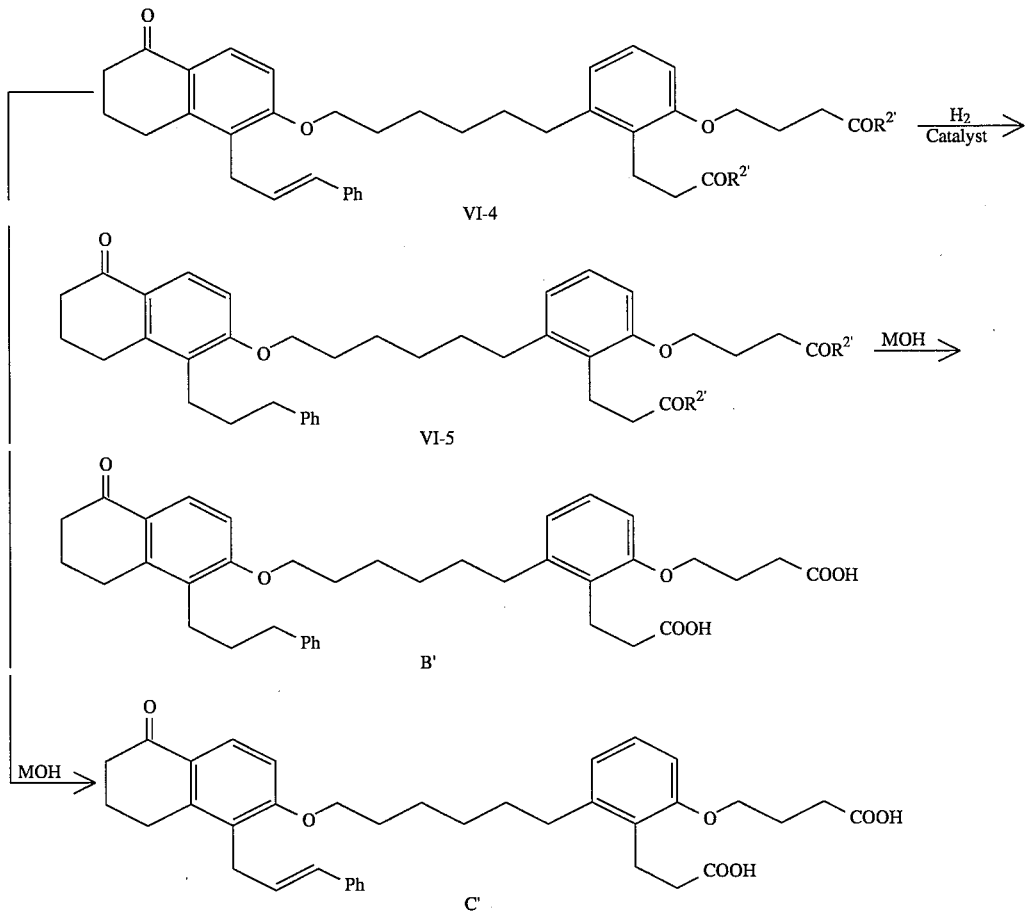

wherein $R^{2'}$, L, and M are as previously defined.

In Reaction Scheme VI, the allyl ether of formula VI-1, a known compound, is thermolyzed in order to effect Claisen rearrangement. It is preferred that this thermolysis be carried out within a temperature range of 180°–230° C. without any solvent, or in a solvent of sufficiently high boiling point such as N,N-diethylaniline. The desired isomeric naphthalenone product of this thermolysis, represented by formula VI-2, can be recovered by recrystallization. The naphthalenone of formula VI-2 is alkylated with the compound of formula I-10 giving the product of formula VI-3, as described in Reaction Scheme II for the conversion of the compound of formula II-6 to the compound of formula II-7. The product of formula VI-3 is recovered by conventional chromatography and is phenylated to give the compound of formula VI-4 as described in Reaction Scheme II for the conversion of the compound of formula II-3 to the compound of formula II-5. The compound of formula VI-4 is recovered by conventional chromatography. Catalytic hydrogenation of the compound of formula VI-4 gives the corresponding compound of formula VI-5 which is recovered by chromatography. This hydrogenation is carried out under conditions described in Reaction Scheme III for the conversion of the compound of formula III-3 to the compound of formula II-7. Saponification of the compound of formula VI-5 affords the corresponding diacid of formula B', recovered by recystallization, and is carried out as described in Reaction Scheme II for the conversion of the compound of formula II-7 to the compound of formula A'. Alternatively, saponification of the compound of formula VI-4 under the same conditions, gives the corresponding diacid of formula C' which is recovered by chromatography or recrystallization.

The invention also relates to salts of the compounds of formula A, B and C when they contain an acidic functionality which lends itself to salt formation with a base. Salts of compounds of formulas A, B and C which have a carboxy group are prepared by the reaction with a non-toxic, pharmacologically acceptable base. In general, any base which will form a salt with a carboxylic acid and whose pharmacological properties will not cause an adverse physiological effect is within the scope of this invention.

Suitable bases include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as, monoalkylamines, dialkylamines, trialkylamines, for example, methylamine, diethylamine, triethylamine or the like, nitrogen containing heterocyclic amines, for example, piperidine or the like. A salt thus produced is the functional equivalent of the corresponding compound of formulas A, B and C wherein $R^2$ is hydroxy and one skilled in the art will appreciate that the variety of salts embraced by the invention is limited only by the criterion that a base employed in forming the corresponding salts be both non-toxic and physiologically acceptable.

The useful activity of the compounds of formula I as leukotriene $B_4$ antagonists can be demonstrated as hereinafter set forth.

Methodology:

$LTB_4$ Receptor Binding Assay

Binding assays can be performed in microliter wells. Isolated human neutrophils in Gey's salt solution are incubated on ice for 45 minutes with 0.5 nM $^3H\text{-}LTB_4$ in the presence or absence of test compounds. Assays are terminated by adding 12 ml of ice cold 50 mM Tris buffer (pH 7.4) followed by rapid filtration under vacuum through GF/C filters. Radioactivity is determined by scintillation counting. Non specific binding is defined as the binding not displaced by 100 fold excess of unlabelled $LTB_4$. Specific binding is defined as the difference between total binding and non-specific binding. Non linear analysis of the binding data is performed using LIGAND (Munson and Rodbard, 1980). $K_i$ (Inhibition Constant) values were determined using the Cheng-Prusoff relationship (Cheng and Prusoff, 1973).

When representative compounds of formulas A, B or C of the invention were tested, the results as set forth in Table I and expressed as inhibition of $^3H\text{-}LTB_4$ binding were obtained.

TABLE 1

| TEST COMPOUND | HUMAN NEUTROPHIL CELLS (KjnM) |
| --- | --- |
| 2-(3-Carboxypropoxy)-6-[6-[[3,4-dihydro-4-oxo-8-(3-phenylpropyl)-2H-1-benzopyran-7-yl]oxy]hexyl]-benzenepropanoic Acid | 1 |
| 2-(3-Carboxypropoxy)-6-[6-[[5,6,7,8-tetrahydro-5-oxo-1-(3-phenylpropyl)-2-naphthalenyl]oxy]hexyl]-benzenepropanoic Acid | 2 |
| (E)-2-(3-Carboxypropoxy)-6-[6-[[5,6,7,8-tetrahydro-5-oxo-1-(3-phenyl-2-propenyl)-2-naphthalenyl]oxy]hexyl]-benzenepropanoic Acid | 1 |

Guinea Pig Bronchoconstriction, In Vivo

Male guinea pigs (Hartley strain), weighing 300 to 500 g are anesthetized with urethane (2 g/kg) intraperitoneally and a polyethylene cannula is inserted into the jugular vein for drug administration. Tracheal pressure is recorded from a cannula inserted into the trachea and connected to a Gould P231D pressure transducer. After surgical preparation of the animals, a period of time is allowed for pulmonary functions to stabilize. Animals are then paralyzed with succinylcholine (1.2 mg/kg, i.v.) and mechanically respirated (Harvard rodent respirator) at 40 breaths/minute and 2.5 cc tidal volume. The test compound is administered p.o., 2 hr prior to leukotriene $B_4$ administration. Propranolol (0.1 mg/kg) is administered intravenously 5 min prior to leukotriene $B_4$ administration. Animals are then challenged with an intermediate constrictory dose of leukotriene $B_4$ (200 µg/kg), delivered intravenously.

The change (cm $H_2O$) between pre and peak ventilatory pressure readings is averaged for 6 control and 6 drug treated animals. The percent inhibition is calculated from the formula:

((Control−Drug Treated)/Control)×100

When representative compounds of formulas A, B and C of the invention were utilized as the test compounds, the following results were obtained:

TABLE 2

| | % inhibition, 0.1 mg/kg test compound dose |
| --- | --- |
| 2-(3-Carboxypropoxy)-6-[6-[[3,4-dihydro-4-oxo-8-(3-phenylpropyl)-2H-1-benzopyran-7-yl]oxy]hexyl]-benzenepropanoic Acid | 67 |
| 2-(3-Carboxypropoxy)-6-[6-[[5,6,7,8-tetrahydro-5-oxo-1-(3-phenylpropyl)-2-naphthalenyl]oxy]hexyl]-benzenepropanoic Acid | 78 |
| (E)-2-(3-Carboxypropoxy)-6-[6-[[5,6,7,8-tetrahydro-5-oxo-1-(3-phenyl-2-propenyl)-2-naphthalenyl]oxy]hexyl]-benzenepropanoic Acid | 64 |

In the practice of the invention, the dose of a compound of formula A, B, C or a salt thereof to be administered and the frequency of administration will be dependent on the potency and duration of activity of the particular compound of formula A, B, C or a salt thereof to be administered and on the route of administration, as well as the severity and nature of the condition and age of the mammal to be treated and the like. Oral doses of a compound of formula A, B or C or a salt thereof contemplated for use in practicing the invention can be in the range of from 2 mg to about 2 g per day, preferably about 2 mg to about 1 gm per day, either as a single dose or in divided doses.

The examples which follow further illustrate the invention.

A compound of formula A, B or C, or a salt or a composition containing a therapeutically effective amount of a compound of formula A, B or C, or a salt thereof can be administered by methods well known in the art. Thus, a compound of formula A, B or C, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil solution or suspension using excipients and carders conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition. For topical administration, they can be administered in the form of an ointment, cream, lotion, powder, gel or the like. Suitable carder materials for topical preparations are glycerides, semi-synthetic and synthetic glycerides, hydrogenated oils, liquid waxes, liquid paraffins, liquid fatty alcohols, sterols, polyethylene glycols, cellulose derivatives, and the like.

It is to be understood that formula C as used herein, includes geometric isomers. The geometric isomers can be separated into the respective E- and Z-isomers utilizing known procedures as further examplified herein.

In the following examples, the "usual work-up" procedure involves three extractions with the specified solvent. The organic extracts were combined, washed with water and saturated brine, dried over anhydrous magnesium sulfate, filtered, and concentrated under water aspirator pressure. The residue was dried to constant weight at 45° C./high vacuum. All reactions except hydrogenations were carried out under an inert atmosphere of nitrogen or argon.

EXAMPLE 1

Preparation of 7-(Phenylmethoxy)-8-(2-propenyl)-4H-1-benzopran-4-one

A mixture of 5.0 g (17.73 mmol) of 1-[2-hydroxy-4-(phenylmethoxy)-3-(2-propenyl)phenyl]ethanone, 2.3 g (19.48 mmol) of dimethylformamide dimethyl acetal, and 5.0 mL of xylene was stirred and heated in a 120°–130° C. oil-bath as methanol was distilled out using a 3 in. Vigreux column, over a 2.5 hr period. The bath temperature was then raised to 150°–160° C. and the reaction mixture was stirred at this temperature for an additional 30 min. The mixture was cooled and concentrated at 60° C./high vacuum. To the viscous, red-brown, oily residue was added 3.7 g (19.48 mmol) of p-toluenesulfonic acid monohydrate and 50 mL of ethanol. The resulting solution was stirred and refluxed for 24 hr, then cooled and diluted with water. Work-up with ether in the usual manner gave a crude product which was recrystallized from hexane-ethyl acetate. There was obtained 3.5 g (67.6%) of 7-(phenylmethoxy)-8-(2-propenyl)-4H-1-benzopyran-4-one as a yellow solid, mp 90°–92° C.

Anal. Calcd for $C_{19}H_{16}O_3$: C, 78.06; H, 5.52. Found: C, 77.97; H, 5.56.

EXAMPLE 2

Preparation of (E)-7-(Phenylmethoxy)-8-(3-phenyl-2-propenyl)-4H-1-benzopyran-4-one A mixture of 8.76 g (30 mmol) of 7-(phenylmethoxy)-8-(2-propenyl)-4H-1-benzopyran-4-one (preceding example), 6.70 g (32.84 mmol) of iodobenzene, 5.11 g (30.84 mmol) of tetraethylammonium chloride, 8.94 g (91.22 mmol) of anhydrous sodium acetate, and 64 mL of dry N,N-dimethylformamide was stirred at room temperature while being purged with a stream of argon. Palladium(II) acetate (0.38 g; 1.7 mmol) was added and stirring was continued at room temperature, for 24 hr. The dark mixture was diluted with water and worked-up with ether in the usual manner (the ether extracts were additionally washed with 12% aqueous sodium bisulfite solution). Recrystallization of the crude product from acetonitrile afforded 6.13 g (55.5%) of the title compound as a brown solid. The analytical specimen was obtained from a separate experiment as yellow crystals, mp 131°–133° C.

Anal. Calcd for $C_{25}H_{20}O_3$: C, 81.50; H, 5.47. Found: C, 81.34; H, 5.10.

EXAMPLE 3

Preparation of 2,3-Dihydro-7-hydroxy-8-(3-phenylpropyl)-4H-1-benzopyran-4-one

A mixture of 6.1 g (16.6 mmol) of (E)-7-(phenylmethoxy)-8-(3-phenyl-2-propenyl)-4H-1-benzopyran-4-one from the preceding example, 1 g of 10% palladium on carbon, 100 mL of methanol, and 300 mL of ethyl acetate was stirred at room temperature, in an atmosphere of hydrogen until approximately one third of the theoretical volume of hydrogen gas was taken up. The catalyst was filtered with suction and the filtrate concentrated in vacuo. The residue was dissolved in 150 mL of methanol and 0.5 g of Raney nickel was added. The hydrogenation was continued with careful monitoring by TLC analysis. When the reduction was essentially complete, the catalyst was filtered with suction and the filtrate concentrated in vacuo. The solid residue (4.75 g) was combined with 6.4 g from another experiment (23.9 mmol scale) and chromatographed on silica gel. Elution with hexane-ethyl acetate mixtures afforded 10.73 g (93.9%) of the title compound as a colorless solid, mp 110°–112° C.

EXAMPLE 4

Preparation of 1,3-Dimethoxy-2-(3-phenylpropyl)benzene.

A solution of 8.70 g (63 mmol) of 1,3-dimethoxybenzene in 164 mL of anhydrous tetrahydrofuran was stirred at −20° C. while 1.6M n-butyllithium in hexane (42.1 mL; 67.2 mmol) was added dropwise, over 20 min. The solution was stirred at −20° C. for 3 hr and then allowed to warm to −5° C. whereupon 15.66 g (63.6 mmol) of 1-iodo-3-phenylpropane was added over 15 min. The reaction mixture was stirred at −5° C. for 1 hr and then at room temperature for 3 d. After being recooled to −5° C., the reaction mixture was decomposed by the addition of 1.5N aqueous sulfuric acid. Water was added and the mixture was worked-up with ether in the usual manner. The residue was treated with 100 mL of hexane and the mixture was filtered. Removal of the solvent in vacuo gave 15.28 g (94.7%) of the title compound as a yellow oil.

EXAMPLE 5

Preparation of 1-[2,4-Dimethoxy-3-(3-phenylpropyl)phenyl]ethanone.

A solution of 15.28 g (59.6 mmol) of 1,3-dimethoxy-2-(3-phenylpropyl)benzene from the preceding example, and 4.68 g (59.6 mmol) of acetyl chloride, in 306 mL of dichloromethane was stirred at −5° to 0° C. and 7.95 g (59.6 mmol) of aluminum chloride was added. The resulting mixture was stirred at −5° to 0° C. for 2 hr and then allowed to warm to room temperature before being poured onto ice. Work-up with ether in the usual manner gave a product which was chromatographed on silica gel. Elution with 7:3 hexane-ether afforded 10.0 g (56.3%) of the title compound as a pale-yellow oil.

EXAMPLE 6

Preparation of 1-[2,4-Dihydroxy-3-(3-phenylpropyl)phenyl]ethanone

A solution of 10.0 g (33.5 mmol) of 1-[2,4-dimethoxy-3-(3-phenylpropyl)phenyl] ethanone from the preceding example in 250 mL of dichloromethane was stirred at −50° C. while 67 mL (67 mmol) of 1M boron tribromide in dichloromethane was added over a 15 min period. The reaction mixture was stirred at −50° C. for 1 hr and at room temperature for 3 days before being poured onto ice. Work-up with 9:1 dichloromethanemethanol in the usual manner gave a product which was chromatographed on silica gel. Elution with hexane-ether mixtures gave 6.69 g (74%) of the title compound as a solid. Recrystallization of a sample from ether-hexane gave colorless solid, mp 120°–122° C.

Anal. Calcd for $C_{17}H_{18}O_3$: C, 75.53; H, 6.71. Found: C, 75.31; H, 6.73.

EXAMPLE 7

Preparation of 1-[2-Hydroxy-4-(phenylmethoxy)-3-(3-phenylpropyl)phenyl]ethanone

A mixture of 6.69 g (24.7 mmol) of 1-[2,4-dihydroxy-3-(3-phenylpropyl)phenyl] ethanone, from the preceding example, 5.35 g (31.3 mmol) of benzyl bromide, 14.9 g (0.108 mol)of anhydrous potassium carbonate, 115 mL of dry N,N-dimethylformamide, and 230 mL of acetone was stirred and refluxed for 8 hr. After being cooled, the slurry was filtered with suction and the solids washed well with acetone. The filtrate and washes were combined and concentrated under reduced pressure to give a yellow oil which was chromatographed on silica gel. There was obtained 5.57 g (62.6%) of the desired monoether as a pale-yellow solid. Recrystallization of a sample from hexane-ethyl acetate gave the title compound as colorless needles, mp 115°–116° C.

Anal. Calcd for $C_{24}H_{24}O_3$: C, 79.97; H, 6.71. Found: C, 79.97; H, 6.80.

EXAMPLE 8

Preparation of 7-(phenylmethoxy)-8-(3-phenylpropyl)-4H-1-benzopyran-4-one

Using the procedure of example 1, 1-[2-hydroxy-4-(phenylmethoxy)-3-(3-phenylpropyl)phenyl]ethanone from the preceding example, was convened into the title compound, a colorless solid, mp 106°–107.5° C. (recrystallized from hexane-ethyl acetate), in 56.7% yield.

Anal. Calcd for $C_{25}H_{22}O_3$: C, 81.05; H, 5.99. Found: C, 81.20; H, 5.99.

EXAMPLE 9

Preparation of 2,3-Dihydro-7-hydroxy-8-(3-phenylpropyl)-4H-1-benzopyran-4-one

Catalytic hydrogenation of 7-(phenylmethoxy)-8-(3-phenylpropyl)-4H-1-benzopyran-4 -one, from the preceding example, was carried out over 10% palladium on carbon at room temperature and 1 atmosphere, in 1:1 methanol-ethyl acetate. The crude product was purified by chromatography on silica gel, eluting with ether-dichloromethane mixtures. The title compound, a colorless solid, mp 110°–112° C. (recrystallized from hexane-ether), was obtained in 44.9% yield.

Anal. Calcd for $C_{18}H_{18}O_3$: C, 76.57; H, 6.43. Found: C, 76.42; H, 6.43.

EXAMPLE 10

Preparation of Trifluoromethanesulfonic Acid 2-Oxo-2H-1-benzopyran-5-yl Ester

A mixture of 1.62 g (10 mmol) of 5-hydroxycoumarin and 10 mL of dry pyridine in 25 mL of dichloromethane was stirred with ice-bath cooling while 4.5 g (16 mmol) of trifluoromethanesulfonic anhydride was added dropwise. The mixture was stirred in the cold for 30 min and then allowed to warm to room temperature and stirred for an additional 30 min before being poured into 3N hydrochloric acid. Work-up with ether in the usual manner gave a yellow solid. Flash chromatography on silica gel, eluting with 2:1 hexane-ethyl acetate afforded 2.6 g (88.4%) of trifluoromethanesulfonic acid 2-oxo-2H-1-benzopyran- 5-yl ester as an off-white solid mp 104°–105° C.

Anal. Calcd for $C_{10}H_5F_3O_5S$: C, 40.83; H, 1.71. Found: C, 40.65; H, 1.59.

EXAMPLE 11

Preparation of rac-5-[6-[(Tetrahydro-2H-pyran-2-yl)oxy]-1-hexynyl]-2H-1 -benzopyran-2-one A mixture of 1.47 g (5 mmol) of trifluoromethanesulfonic acid 2-oxo-2H-1-benzopyran- 5-yl ester (preceding example), 1.0 g (5.5 mmol) of rac-6-[(tetrahydro-2H-pyran-2-yl)oxy]-1-hexyne, 75 mg of cuprous iodide, 0.3 g (0.428 mmol) of dichloro-bis(triphenylphosphine)palladium(II), 7.5 mL of triethylamine, and 35 mL of dry N,N-dimethylformamide was stirred and heated at 100° C. for 24 hr. The reaction mixture was cooled, poured into water, and worked-up with ether in the usual manner. The dark-brown, oily residue was flash chromatographed on silica gel. Elution with 2:1 hexane-ethyl acetate gave 1.09 g (67%) of rac-5-[6-[(tetrahydro-2H-pyran-2-yl)oxy]-1-hexynyl]-2H-1-benzopyran-2-one as an orange oil.

EXAMPLE 12

Preparation of rac-(E)-3-[2-Hydroxy-6-[6-[(tetrahydro-2H-pyran-2-yl)oxy]-1-hexynyl]phenyl]-2-propenoic Acid Methyl Ester A solution of 1.09 g (3.3 mmol) of rac-5-[6-[(tetrahydro-2H-pyran-2-yl)oxy]-1-hexynyl]-2H-1-benzopyran-2-one (preceding example) and 1.8 mL (7.9 mmol) of 25% methanolic sodium methoxide in 5 mL of methanol was stirred and refluxed for 24 hr and then concentrated under reduced pressure. The residue was treated with 1N hydrochloric acid and worked-up with ethyl acetate in the usual manner (the organic extracts were additionally washed with saturated aqueous sodium bicarbonate). The residue was purified by flash chromatography on silica gel, eluting with 2:1 hexane-ether. There was obtained 0.7 g (59%) of rac-(E)-3-[2-hydroxy-6-[6-[(tetrahydro-2H-pyran-2-yl)oxy]-1-hexynyl] phenyl]-2-propenoic acid methyl ester as a yellow oil. Trituration of a sample prepared in this way with hexane gave a colorless solid, mp 66°–67.5° C.

Anal. Calcd for $C_{21}H_{26}O_5$: C, 70.37; H, 7.31. Found: C, 70.24; H, 7.33.

EXAMPLE 13

Preparation of rac-(E)-4-[2-(3-Methoxy-3-oxo-1-propenyl)-3-[6-[(tetra-hydro- 2H-pyran-2-yl)oxy]-1-hexynyl]phenoxy]butanoic Acid Ethyl Ester A mixture of 7.16 g (20 mmol) of rac-(E)-3-[2-hydroxy-6-[6-[(tetrahydro-2 H-pyran-2-yl)oxy]-1-hexynyl]phenyl]-2-propenoic acid methyl ester (preceding example), 4.37 g (22.4 mmol) of ethyl 4-bromobutyrate, 8.32 g (60.29 mmol) of anhydrous, granular potassium carbonate, and 50 mL of dry dimethyl sulfoxide was stirred at room temperature for 23 hr. The resulting mixture was diluted with ether and worked-up in the usual manner. There was obtained 9.73 g of rac-(E)-4-[2-(3-methoxy-3-oxo-1-propenyl)-3-[6-[(tetrahydro-2H-pyran-2-yl)oxy]-1-hexynyl]phenoxy]butanoic acid ethyl ester as a yellow oil containing ca. 10% of ethyl 4-bromobutyrate (NMR analysis). This material was used without further purification.

EXAMPLE 14

Preparation of rac-2-(4-Ethoxy-4-oxobutoxy)-6-[6-[(tetrahydro-2H-pyran-2-yl)oxy]hexyl]benzenepropanoic Acid Methyl Ester A 9.73 g (ca. 20 mmol) sample of crude rac-4-[2-(3-methoxy-3-oxo-1-propenyl)-3 -[6-[(tetrahydro-2H-pyran-2-yl)oxy]-1-hexynyl]phenoxy]butanoic acid ethyl ester from the preceding example was hydrogenated in 275 mL of ethyl acetate, over 0.75 g of 10% palladium on carbon, at room temperature and 1 atmosphere, for 24 hr. rac-2-(4-Ethoxy-4 -oxobutoxy)-6-[6-[(tetrahydro-2H-pyran-2-yl)oxy]hexyl] benzenepropanoic acid methyl ester, an oil, was isolated by filtration of the catalyst and concentration of the filtrate, in quantitative yield (9.74 g).

EXAMPLE 15

Preparation of 2-(6-Hydroxyhexyl)-6-(4-methoxy-4-oxobutoxy)benzenepropanoic Acid Methyl Ester A solution of 9.74 g (ca. 20 mmol) of rac-2-(4-ethoxy-4-oxobutoxy)-6-[6 -[(tetrahydro-2H-pyran-2-yl)oxy]hexyl] benzenepropanoic acid methyl ester from the preceding example, and 0.53 g of p-toluenesulfonic acid monohydrate, in 270 mL of methanol was stirred and refluxed for 21.5 hr. Most of the solvent was removed in vacuo and the residue was dissolved in ether. The ether solution was washed with saturated sodium bicarbonate solution and processed in the usual manner giving an oil. This material was chromatographed on 200 g of silica gel, eluting with hexane-ethyl acetate mixtures. There was obtained 7.03 g (92.5%) of 2-(6-hydroxyhexyl)-6-(4-methoxy-4-oxobutoxy)benzenepropanoic acid methyl ester as a colorless oil.

EXAMPLE 16

Preparation of 2-(4-Methoxy-4-oxobutoxy)-6-[6-[(methylsulfonyl)oxy]hexyl]benzenepropanoic Acid Methyl Ester A solution of 7.03 g (18.5 mmol) of 2-(6-hydroxyhexyl)-6-(4-methoxy-4-oxobutoxy)benzenepropano acid methyl ester from the preceding example, and 22.5 mL of triethylamine, in 67.5 mL of ethyl acetate was stirred with ice-bath cooling while 6.75 mL (87.25 mmol) of methanesulfonyl chloride was added dropwise over a 10 min period. The resulting dense slurry was stirred at 0°–5° C. for 10 min and then kept at 0°–5° C. for 21 hr The mixture was treated with 100 mL of water and 100 mL of ether while still cold. Work-up with ether in the usual manner (the organic extracts were additionally washed with 1N aqueous hydrochloric acid and saturated aqueous sodium bicarbonate solution) gave 8.45 g (99.7%) of 2-(4-methoxy-4-oxobutoxy)-6-[6-[(methylsulfonyl)oxy]hexyl] -benzenepropanoic acid methyl ester as a pale-yellow oil which was used without further purification.

EXAMPLE 17

Preparation of 2-(6-Iodohexyl)-6-(4-methoxy-4-oxobutoxy)benzenepropanoic Acid Methyl Ester A mixture of 10.81 g (ca. 23.37 mmol) of crude 2-(4-methoxy-4-oxobutoxy)-6-[6 [(methylsulfonyl)oxy]hexyl] benzenepropanoic acid methyl ester (preceding example), 7.01 g (46.7 mmol) of anhydrous sodium iodide, and 44 mL of dry acetonitrile was stirred at room temperature for 17 hr and then refluxed for 3.5 hr. After being cooled, the mixture was diluted with 200 mL of ether and filtered with suction. The solids were washed thoroughly with ether. The filtrate and washes were combined and washed with 12% aqueous sodium bisulfite, and work-up was completed in the usual manner. There was obtained 11.14 g (97.3%) of 2-(6-iodohexyl)-6-(4-methoxy-4-oxobutoxy)benzenepropanoic acid methyl ester as a yellow oil.

EXAMPLE 18

Preparation of 2-[6-[(3,4-Dihydro-4-oxo-8-(3-phenylpropyl)-2H-1 -benzopyran-7-yl)oxy]hexyl]-6-(4-methoxy-4-oxobutoxy)benzenepropanoic Acid Methyl Ester A mixture of 12.25 g (25 mmol) of 2-(6-iodohexyl)-6-(4-methoxy-4 -oxobutoxy)benzenepropanoic acid methyl ester (preceding example), 7.1 g (25.2 mmol) of 2,3 -dihydro-7-hydroxy-8-(3-phenylpropyl)-4H-1-benzopyran-4-one (example 9), 8.3 g (60 mmol) of anhydrous potassium carbonate, and 60 mL of dry acetonitrile was stirred and refluxed for 22 hr. After being cooled, the mixture was diluted with ether and filtered with suction. The solids were washed well with ether. The filtrate and washes were combined and concentrated in vacuo giving 16.5 g of a yellow oil. This material was chromatographed on silica gel, eluting with hexane-ethyl acetate mixtures. There was obtained 13.75 g (85.4%) of pure title dimethyl ester, as an oil.

EXAMPLE 19

Preparation of 2-(3-Carboxypropoxy)-6-[6-[[3,4-dihydro-4-oxo-8-(3 -phenylpropyl)-2H-1-benzopyran-7-yl]oxy]hexyl] benzenepropanoic Acid The diester from the preceding example (13.75 g; 21.35 mmol) was saponified by stirring in 500 mL of tetrahydrofuran containing 60 mL of 3N aqueous lithium hydroxide, at room temperature, for 24 hr. The tetrahydrofuran was removed in vacuo and the residue was dissolved in water and acidified with 3N aqueous hydrochloric acid. The mixture was worked-up with ethyl acetate in the usual manner giving an off-white solid. This material was purified by flash chromatography on silica gel, eluting with 96:2.5:1 chloroform-methanol-acetic acid. Recrystallization of the combined, pure diacid fractions from acetonitrile gave 10.4 g (79%) of the title diacid, as a colorless solid, mp 104°–106° C.

Anal. Calcd for $C_{37}H_{44}O_8$: C, 72.06; H, 7.19. Found: C, 71.74; H, 7.27.

EXAMPLE 20

Preparation of 3,4-Dihydro-6-hydroxy-5-(2-propenyl)-1(2H)-naphthalenone

A solution of 12.51 g (61.93 mmol) of 3,4-dihydro-6-(2-propenyloxy)-1(2H)-naphthalenone in 125 mL of N,N-diethylaniline was stirred and heated in a 225°–230° C. oil bath, for 20.5 hr. The resulting dark-amber solution was cooled and poured into 300 mL of cold 3N HCl. The mixture was worked-up with ether in the usual manner giving 12.29 g of a yellow solid which was a mixture of the 5- and 7-allyl isomeric hydroxy naphthalenones. This material was recrystallized from ethyl acetate giving the pure 5-allyl isomer in 60% yield, in several crops. The analytical specimen was a yellow solid, mp 145°–148° C.

Anal. Calcd for $C_{13}H_{14}O_2$: C, 77.20; H, 6.98. Found: C, 76.97; H, 7.00.

EXAMPLE 21

Preparation of 2-(4-Methoxy-4-oxobutoxy)-6-[6-[[5,6,7,8-tetrahydro-5 -oxo-1-(2-propenyl)-2-naphthalenyl]oxy] hexyl]benzenepropanoic Acid Methyl Ester A mixture of 3.5 g (17.3 mmol) of 3,4-dihydro-6-hydroxy-5-(2-propenyl)-1(2H)-naphthalenone (from example 20), 8.5 g (17.35 mmol) of 2-(6-iodohexyl)-6-(4-methoxy-4-oxobutoxy)benzenepropanoic acid methyl ester (example 17), 5.8 g (42.0 mmol) of anhydrous potassium carbonate, and 40 mL of anhydrous acetonitrile was stirred and refluxed for 24 hr. The resulting mixture was cooled, diluted with ether, and filtered with suction. The solids were washed thoroughly with ether and then the filtrate and washes were combined, and concentrated in vacuo. The residue was purified by chromatography on silica gel, eluting with hexane-ethyl acetate mixtures. The title diester was obtained in quantitative yield (9.73 g), as a pale-yellow oil.

EXAMPLE 22

Preparation of (E)-2-(4-Methoxy-4-oxobutoxy)-6-[6-[[5,6,7,8-tetrahydro-5-oxo-1-(3-phenyl-2-propenyl)-2-naphthalenyl]oxy]hexyl]benzenepropanoic Acid Methyl Ester A mixture of 9.73 g (17.23 mmol) of 2-(4-methoxy-4-oxobutoxy)-6-[6-[[5,6,7,8 -tetrahydro-5-oxo-1-(2-propenyl)-2-naphthalenyl]oxy]hexyl]benzenepropanoic acid methyl ester from example 21, 3.84 g ( 18.86 mmol) of iodobenzene, 2.93 g ( 17.72 mmol) of tetraethylammonium chloride, 5.13 g (52.25 mmol) of anhydrous sodium acetate, and 37 mL of dry N,N-dimethylformamide was stirred at room temperature while being purged with a stream of argon. Palladium(II) acetate (0.216 g; 0.96 mmol) was added and stirring was continued at room temperature, for 22 hr. The dark-brown mixture was treated with ether and water and filtered through Celite. The filtrate was worked-up with ether in the usual manner (the ether extract was additionally washed with 12% aqueous sodium bisulfite solution) giving 11.54 g of crude product. This material was chromatographed on 350 g of silica gel, eluting with hexane-ethyl acetate mixtures. There was obtained 8.63 g (78%) of the title olefin as a pale-yellow oil.

EXAMPLE 23

Preparation of 2-(4-Methoxy-4-oxobutoxy)-6-[6-[[5,6,7,8-tetrahydro-5 -oxo-1-(3-phenylpropyl)-2-naphthalenyl]oxy] hexyl]benzenepropanoic Acid Methyl Ester (E)-2-(4-Methoxy-4-oxobutoxy)-6-[6-[[5,6,7,8-tetrahydro-5-oxo-1-(3-phenyl- 2-propenyl)-2-naphthalenyl]oxy] hexyl]benzenepropanoic acid methyl ester (0.54 g; 0.84 mmol), from the preceding example, was hydrogenated in 25 mL of ethyl acetate, over 0.1 g of 10% palladium on carbon, at room temperature and 1 atmosphere, for 2 hr. The catalyst was filtered and the filtrate concentrated to give 0.52 g (96%) of the title diester as a pale-yellow oil.

EXAMPLE 24

Preparation of 2-(3-Carboxypropoxy)-6-[6-[[5,6,7,8-tetrahydro-5-oxo-1 -(3-phenylpropyl)-2-naphthalenyl]oxy] hexyl]benzenepropanoic Acid 2-(4-Methoxy-4-oxobutoxy)-6-[6-[[5,6,7,8-tetrahydro-5-oxo-1-(3 -phenylpropyl)-2-naphthalenyl]oxy]hexyl]benzenepropanoic acid methyl ester from the preceding example (0.52 g; 0.8 mmol) was saponified by stirring in 22 mL of tetrahydrofuran containing 2.6 mL of 3N aqueous lithium hydroxide, at room temperature, for 24 hr. The mixture was concentrated in vacuo. The residue was dissolved in water and acidified with 3N aqueous hydrochloric acid. Work-up with ether in the usual manner gave a viscous, oily residue which was purified by flash chromatography on silica gel, eluting with 90:10:5 toluene-ethyl acetate-acetic acid. Recrystallization of the combined pure fractions from hexane-ethyl acetate gave the title diacid in 73% yield (0.36 g), as a colorless solid, mp 89°–91° C.

Anal. Calcd for $C_{38}H_{46}O_7$: C, 74.24; H, 7.54. Found: C, 74.15; H, 7.75.

EXAMPLE 25

Preparation of 2-(4-Methoxy-4-oxobutoxy)-6-[6-[(4-oxo-8-(2-propenyl)-4H-1-benzopyran-7-yl)oxy]hexyl]benzenepropanoic Acid Methyl Ester.

To a slurry of 202 mg( 5.05 mmol) of 60% sodium hydride-mineral oil dispersion (pre-washed with penlane) in 3 mL of anhydrous N,N-dimethylformamide was added a solution of 0.77 g (3.81 mmol) of 7-hydroxy-8-(2-propenyl)-4H-1-benzopyran-4-one in 12 mL of anhydrous N,N-dimethylformamide, over a 1 min period. The mixture was stirred at room temperature for 15 min whereupon a solution of 2.1 g (4.29 mmol) of 2-(6 -iodohexyl)-6-(4-methoxy-4-oxobutoxy)benzenepropanoic acid methyl ester (example 17) in 15 mL of anhydrous N,N-dimethylformamide was added over a 1 min period. The resulting mixture was stirred at room temperature for 3 hr before being treated with ice-water, and worked-up with ethyl acetate in the usual manner. The oily product was chromatographed on silica gel, eluting with hexane-ethyl acetate mixtures. There was obtained 1.7 g (79.1%) of the title compound as a yellow oil.

EXAMPLE 26

Preparation of 2-(4-Methoxy-4-oxobutoxy)-6-[6-[(4-oxo-8-(3-phenyl-2 -propenyl)-4H-1-benzopyran-7-yl)oxy]hexyl] benzenepropanoic Acid Methyl Ester.

Using the procedure of example 22, 2-(4-methoxy-4-oxobutoxy)-6-[6-[(4-oxo-8-(2-propenyl)-4H-1-benzopyran-7-yl)oxy]hexyl]benzenepropanoic acid methyl ester from the preceding example was convened into the title compound, a pale-yellow oil, in 73% yield.

EXAMPLE 27

Preparation of 2-[6-[(3,4-Dihydro-4-oxo-8-(3-phenylpropyl)-2H-1-benzopyran-7-yl)oxy]hexyl]-6-(4-methoxy-4-oxobutoxy)benzenepropanoic Acid Methyl Ester Using the procedure of example 23, 2-(4-methoxy-4-oxobutoxy)-6-[6-[(4-oxo-8-(3-phenyl-2-propenyl)-4H-1-benzopyran-7-yl)oxy]hexyl]benzenepropanoic acid methyl ester from the preceding example was catalytically hydrogenated giving the title compound, as an oil.

EXAMPLE 28

Preparation of 2-(3-Phenylpropenylidene)-1,3-cyclohexanedione.

A solution of 11.2 g (0.1 mol) of 1,3-cyclohexanedione in 110 mL of ethanol was stirred at room temperature while 1 mL of piperidine was added followed by the dropwise addition of 13 mL (0.103 mol) of trans-cinnamaldehyde over a 2 min period. The resulting mixture was stirred at room temperature for 2 hr and then in an ice-bath for 1 hr. The resulting yellow slurry was filtered with suction and the solid dried under high vacuum giving 13.9 g (61.5%) of the title dione. Recrystallization of a sample of this material from ethyl acetate gave yellow solid, mp 115.5°–118° C.

Anal. Calcd for $C_{15}H_{14}O_2$: C, 79.62; H, 6.24. Found: C, 79.46; H, 6.34.

EXAMPLE 29

Preparation of 2-(3-Phenylpropyl)-1,3-cyclohexanedione.

A mixture of 6.8 g (30 mmol) of 2-(3-phenylpropenylidene)-1,3-cyclohexanedione from the preceding example, 0.7 g of 10% palladium on carbon, and 150 mL of ethyl acetate was stirred at room temperature, in an atmosphere of hydrogen, until gas uptake ceased. The catalyst was filtered with suction and the filtrate was concentrated in vacuo giving 6.7 g (97%) of the title dione as an off-white solid which was used without further purification.

EXAMPLE 30

Preparation of 3-(2-Cyanoethoxy)-2-(3-phenylpropyl)-2-cyclohexenol-1-one.

A mixture of 6.7 g (29 mmol) of 2-(3-phenylpropyl)-1,3-cyclohexanedione from the preceding example, 9.9 mL (0.145 mol) of 3-hydroxypropionitrile, 0.3 g of p-toluenesulfonic acid monohydrate, and 110 mL of toluene was stirred and refluxed with water removal by means of a Dean-Stark trap, for 3 hr. The mixture was cooled, diluted with ethyl acetate, and washed with saturated, aqueous sodium bicarbonate solution. Work-up was completed in the usual manner giving 9.3 g of a yellow oil. This material was chromatogrphed on silica gel. Elution with hexane-ethyl acetate mixtures afforded 5.9 g (71.6%) of the title compound as a yellow oil.

EXAMPLE 31

Preparation of 3-(2-Cyanoethoxy)-2-(3-phenylpropyl)phenol.

To a stirred solution of 6.7 g (23.7 mmol) of 3-(2-cyanoethoxy)-2-(3-phenylpropyl)-2-cyclohexen-1-one (preceding example) in 75 mL of dichloromethane, cooled to 0°–5° C. was added 6.8 g (23.8 mmol) of 1,3-dibromo-5,5-dimethylhydantoin. After being stirred for 30 min in the cold, 50 mL of saturated aqueous sodium bisulfite solution was added. Work-up with dichloromethane in the usual manner gave 9.3 g of a yellow oil. This material was dissolved in 125 mL of toluene and 7.1 g (63.4 mmol) of 1,4-diazabicyclo[2.2.21]octane was added. The mixture was stirred and refluxed for 30 min before being cooled and treated with 2N hydrochloric acid. Work-up with ethyl acetate in the usual manner gave an orange oil which was chromatographed on silica gel. Elution with hexane-ethyl acetate mixtures gave 3.5 g (52.6%) of the title phenol as a yellow oil.

EXAMPLE 32

Preparation of 2,3-Dihydro-7-hydroxy-8-(3-phenylpropyl)-4H-1-benzopyran-4-one

A mixture of 3.5 g (12.5 mmol) of 3-(2-cyanoethoxy)-2-(3-phenylpropyl)phenol (preceding example), 16 mL of 85% phosphoric acid, and 7.7 mL of acetic acid was stirred and heated at 125° C. for 23 hr. After being cooled, the mixture was diluted with water and worked-up with ethyl acetate in the usual manner giving 4 g of a red oil. This material was chromatographed on silica gel. Elution with hexane-ethyl acetate mixtures afforded 2.3 g (65.2%) of the title compound as a yellow solid.

EXAMPLE 33

Preparation of (E)-2-(3-Carboxypropoxy)-6-[6-[[5,6,7,8-tetrahydro-5-oxo-1-(3-phenyl-2-propenyl)-2-naphthalenyl]oxy]hexyl]benzenepropanoic Acid (E)-2-(4-methoxy-4-oxobutoxy)-6-[6-[[5,6,7,8-tetrahydro-5-oxo-1-(3-phenyl-2-propenyl)-2-naphthalenyl]oxy]hexyl]benzenepropanoic acid methyl ester (from example 22 was saponified using the procedure of example 19, giving the title diacid in 82% yield, as a colorless solid, mp 102°–104° C., recrystallized from hexane-ethyl acetate.

Anal. Calcd for $C_{38}H_{44}O_7$: C, 74.49; H, 7.24. Found: C, 74.28; H, 7.14.

EXAMPLE 34

WET GRANULATION FORMULATION

| Ingredients | mg/tablet | | | |
|---|---|---|---|---|
| 1. 2-(3-Carboxypropoxy)-6-[6-[[3,4-dihydro-4-oxo-8-(3-phenylpropyl)-2H-1-benzopyran-7-yl]oxy]hexyl]benzenepropanoic Acid | 0.1 | 0.5 | 5.0 | 5.0 |
| 2. Lactose Anhydrous DTG | 106.9 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Stearate | 1.0 | 1.0 | 1.0 | 2.0 |
| TOTAL | 130.0 | 130.0 | 130.0 | 160.0 |

Manufacturing Procedure:

1) Dissolve Item 1 in a suitable solvent such as alcohol.
2) Spread the solution in Step 1 over Item 2, dry.
3) Add Items 3 and 4 and mix for 10 minutes.
4) Add magnesium stearate and mix for 3 minutes and compress.

EXAMPLE 35

CAPSULE FORMULATION

| Ingredients | mg/capsule | | | |
|---|---|---|---|---|
| 1. 2-(3-Carboxypropoxy)-6-[6-[[5,6,7,8-tetrahydro-5-oxo-1-(3-phenylpropyl)-2-naphthalenyl]oxy]hexyl]benzenepropanoic Acid | 0.1 | 0.5 | 5.0 | 25.0 |
| 2. Lactose Hydrous | 168.9 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 2.0 |
| TOTAL | 200.0 | 200.0 | 200.0 | 200.0 |

Manufacturing Procedure:

1) Mix Items 1, 2 and 3 in a suitable mixer for 30 minutes.
2) Add Items 4 and 5 and mix for 3 minutes.
3) Fill into suitable capsule.

EXAMPLE 36

TABLET FORMULATION (Wet Granulation)

| | | mg/tablet |
|---|---|---|
| Item | Ingredient | 100 mg | 500 mg |
| 1. | (E)-2-(3-Carboxypropoxy)-6-[6-[[5,6,7,8-tetrahydro-5-oxo-1-(3-phenyl-2-propenyl)-2-naphthalenyl]oxy]hexyl]benzenepropanoic Acid | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | TOTAL | 167 | 836 |

Manufacturing Procedure:

1) Mix Items 1, 2, 3 and 4 and granulate with water.

2) Dry the granulation at 50° C.

3) Pass the granulation through suitable milling equipment.

4) Add Item 5 and mix for three minutes; compress on a suitable press.

EXAMPLE 37

CAPSULE FORMULATION

| | | mg/tablet | |
|---|---|---|---|
| Item | Ingredient | 100 mg | 500 mg |
| 1. | 2-(3-Carboxypropoxy)-6-[6-[[3,4-dihydro-4-oxo-8-(3-phenylpropyl)-2H-1-benzopyran-7-yl]oxy]hexyl]benzenepropanoic Acid | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | TOTAL | 117 | 582 |

Manufacturing Procedure:

1) Mix Items 1, 2, and 3 and wet granulate with water. Dry at 45° C. overnight.

2) Mill through suitable screen using appropriate milling equipment.

3) Add Items 4 and 5 and mix for five minutes.

EXAMPLE 38

INHALATION AEROSOL FORMULATION (SUSPENSION)

| Item | Ingredients | % w/w |
|---|---|---|
| 1. | 2-(3-Carboxypropoxy)-6-[6-[[5,6,7,8-tetrahydro-5-oxo-1-(3-phenylpropyl)-2-naphthalenyl]-oxy]hexyl]benzenepropanoic Acid | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing Procedure:

1) Mix Items 1 and 2 into 4 and homogenize.

2) Fill the concentrate suspension from Step 1 into a suitable can and place in valve and crimp to seal container.

3) Pressure-fill a 80:20 mixture of Items 3 and 5.

NOTE: A suitable valve may be used to deliver 25 to 100 microliters in volume.

EXAMPLE 39

OIL-IN-WATER TOPICAL CREAM

| Item | Ingredients | % w/w |
|---|---|---|
| 1. | (E)-2-(3-carboxypropoxy)-6-[6-[[5,6,7,8-tetrahydro-5-oxo-1-(3-phenyl-2-propenyl)-2-naphthalenyl]oxy]hexyl]benzenepropenoic Acid | 0.000001–2.00 |
| 2. | Cetyl Alcohol | 1.50 |
| 3. | Stearyl Alcohol | 2.50 |
| 4. | Span 60 (sorbitan monostearate) | 2.00 |
| 5. | Mineral oil, light | 4.00 |
| 6. | Medium Chain Triglyceride | 3.00 |
| 7. | Arlacel 165 (Glyceryl monostearate and polyoxyethylene glycol stearate blend) | 4.00 |
| 8. | Polysorbate 60 | 1.00 |
| 9. | Propylene Glycol | 5.00 |
| 10. | Benzyl Alcohol | 1.00 |
| 11. | Butylated Hydroxyanisole (BHA) | 0.02 |
| 12. | Sorbitol Solution | 2.00 |
| 13. | Water q.s. to | 100.00 |

The items are mixed in a known manner.

We claim:

1. A compound selected from the group consisting of compounds of the formula:

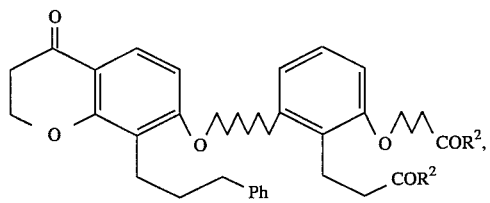

A

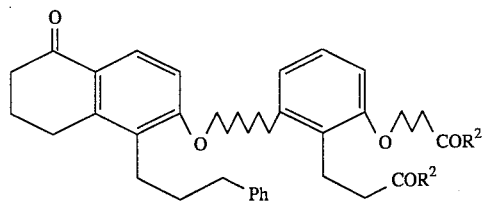

B

, and

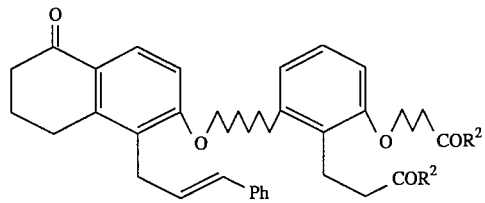

C wherein $R^2$, each occurrence, independently, is hydroxy, lower alkoxy or $NR^3R^4$, wherein $R^3$ and $R^4$, independently, are hydrogen or lower alkyl, and Ph is phenyl and for the compound of formula C, its geometric isomer, and, when $R^2$ is hydroxy, a pharmaceutically acceptable salt thereof with a base.

2. A compound according to claim 1 of formula A.

3. A compound according to claim 1, wherein the compound is 2-(3 -carboxypropoxy)-6-[6-[[3,4-dihydro-4-oxo-8-(3-phenylpropyl)-2H-1-benzopyran-7-yl]oxy]hexyl]benzenepropanoic Acid.

4. A compound according to claim 1, wherein the compound is 2-(3 -carboxypropoxy)-6-[6-[[5,6,7,8-tetrahydro-5-oxo-1-(3-phenylpropyl)-2-naphthalenyl]oxy]hexyl]benzenepropanoic Acid.

5. A compound according to claim 1, wherein the compound is (E)-2-(3 -carboxypropoxy)-6-[6-[[5,6,7,8-tetrahydro-5-oxo-1-(3-phenyl-2-propenyl)-2-naphthalenyl]oxy] hexyl]benzenepropanoic Acid.

6. A pharmaceutical composition which comprises an effective amount of a compound selected from the group consisting of compounds of the formula:

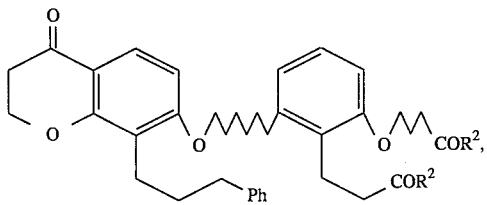

A

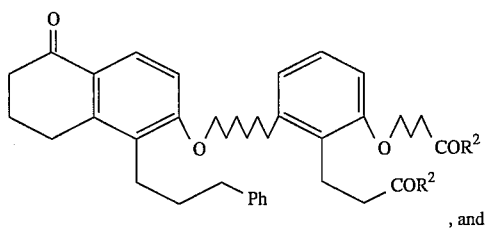

B

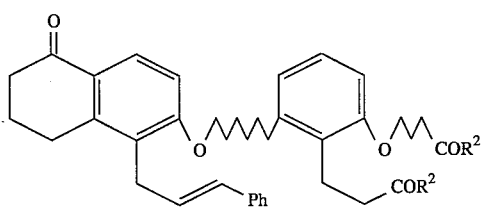

C wherein

R², each occurrence, independently, is hydroxy, lower alkoxy or NR³R⁴, wherein R³ and R⁴, independently, are hydrogen or lower alkyl, and Ph is phenyl and for the compound of formula C, its geometric isomer, and, when R² is hydroxy, a pharmaceutically acceptable salt thereof with a base, and an inert carrier.

7. A pharmaceutical composition according to claim 6, wherein the compound is of formula A.

8. A pharmaceutical composition according to claim 6, wherein the compound is 2-(3-carboxypropoxy)-6-[6-[[3,4-dihydro-4-oxo-8-(3-phenylpropyl)-2H-1-benzopyran-7-yl]-oxy]hexyl]benzenepropanoic Acid.

9. A pharmaceutical composition according to claim 6, wherein the compound is 2-(3-carboxypropoxy)-6-[6-[[5,6,7,8-tetrahydro-5-oxo-1-(3-phenylpropyl)- 2-napthleny]oxy] hexyl]benzenepropanoic Acid.

10. A pharmaceutical composition according to claim 6, wherein the compound is (E)-2-(3-carboxypropoxy)-6-[6-[[5,6,7,8-tetrahydro-5-oxo-1-(3-phenyl-2 -propenyl)-2-naphthalenyl]oxy]hexyl]benzenepropanoic Acid.

11. A method of inhibiting the biological activity of leukotriene B₄ which comprises administering to a host requiring such inhibitory treatment an effective amount of a compound selected from a group of compounds of the formulas

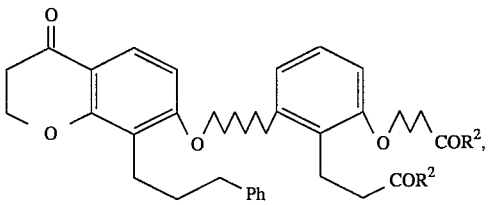

A

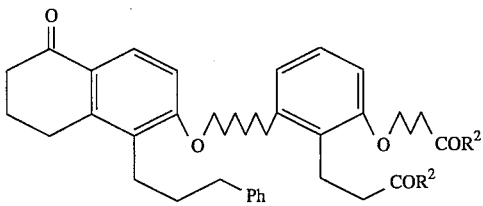

B

, and

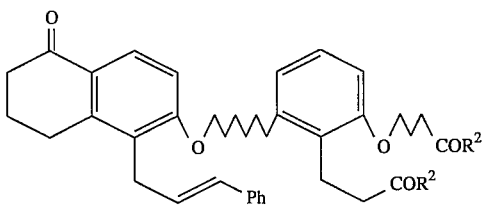

C wherein

R², each occurrence, independently, is hydroxy, lower alkoxy or NR³R⁴, wherein R³ and R⁴, independently, are hydrogen or lower alkyl, and Ph is phenyl and, for the compound of formula C, its geometric isomer, and, when R² is hydroxy, a pharmaceutically acceptable salt thereof with a base.

12. A method according to claim 11, wherein the compound is of formula A.

13. A method according to claim 11, wherein the compound is 2-(3 -carboxypropoxy)-6-[6-[[3,4-dihydro-4-oxo-8-(3-phenylpropyl)-2H-1-benzopyran-7-yl]-oxy]hexyl]benzenepropanoic Acid.

14. A method according to claim 11, wherein the compound is 2-(3 -carboxypropoxy)-6-[6-[[5,6,7,8-tetrahydro-5-oxo-1-(3-phenylpropyl)-2-naphthalenyl]oxy]hexyl]benzenepropanoic Acid.

15. A method according to claim 11, wherein the compound is (E)-2-(3 -carboxypropoxy)-6-[6-[[5,6,7,8-tetrahydro-5-oxo-1-(3-phenyl-2-propenyl)-2-naphthaleny] oxy] hexyl]benzenepropanoic Acid.

16. A method according to claim 11, wherein inhibiting the biological activity of leukotriene B₄ is useful to treat asthma.

17. A method according to claim 11, wherein inhibiting the biological activity of leukotriene B₄ is useful to treat inflammatory bowel disease.

18. A method according to claim 11 wherein inhibiting the biological activity of leukotriene B₄ is useful to treat dermatitis.

19. A method according to claim 11, wherein inhibiting the biological activity of leukotriene B₄ is useful to treat chronic obstructive pulmonary disease.

20. A method according to claim 11, wherein inhibiting the biological activity of leukotriene B₄ is useful to treat arthritis.

* * * * *

UNITED STATES PATENT AND TRADEMARK OFFICE
CERTIFICATE OF CORRECTION

PATENT NO. : 5,457,124
DATED : October 10, 1995
INVENTOR(S) : Noal Cohen, Andrzej R. Daniewski, Ferdinand K. Lee, Keith A. Yagaloff It is certified that error appears in the above-identified patent and that said Letters Patent is hereby corrected as shown below:

- Claim 5, Column 31, lines 9-11: "(E)-2-(3-carboxypropoxy)-6-[6-[[5,6,7,8-tetrahydro-5-oxo-1-(3-phenyl-2-propenyl)-2-naphthalenyl]oxy]hexyl] benzenepropanoic Acid." should read --- (E)-2-(3-carboxypropoxy)-6-[6-[[5,6,7,8-tetrahydro-5-oxo-1-(3-phenyl-2-propenyl)-2-naphthalenyl]oxy]hexyl] benzenepropanoic Acid. --- .

- Claim 9, Column 31, line 60: "napthlenyl]oxy]" should read --- naphthalenyl]oxy] --- .

UNITED STATES PATENT AND TRADEMARK OFFICE
CERTIFICATE OF CORRECTION

PATENT NO. : 5,457,124

DATED : October 10, 1995

INVENTOR(S) : Noal Cohen, Andrzej R. Daniewski, Ferdinand K. Lee, Keith A. Yagaloff It is certified that error appears in the above-identified patent and that said Letters Patent is hereby corrected as shown below:

IN THE CLAIMS - (Continued)

- Claim 10, Column 31, lines 63-65: "(E)-2-(3-carboxypropoxy)-6-[6-[[5,6,7,8-tetrahydro-5-oxo-1-(3-phenyl-2-propenyl)-2-naphthalenyl]oxy]hexyl] benzenepropanoic Acid." should read (E)-2-(3-carboxypropoxy)-6-[6-[[5,6,7,8-tetrahydro-5-oxo-1-(3-phenyl-2-propenyl)-2-naphthalenyl]oxy]hexyl] benzenepropanoic Acid. --- .

- Claim 15, Column 32, lines 49-52: "(E)-2-(3-carboxypropoxy)-6-[6-[[5,6,7,8-tetrahydro-5-oxo-1-(3-phenyl-2-propenyl)-2-naphthalenyl]oxy]hexyl] benzenepropanoic Acid." should read (E)-2-(3-carboxypropoxy)-6-[6-[[5,6,7,8-tetrahydro-5-oxo-1-

UNITED STATES PATENT AND TRADEMARK OFFICE
CERTIFICATE OF CORRECTION

PATENT NO. : 5,457,124

DATED : October 10, 1995

INVENTOR(S) : Noal Cohen, Andrzej R. Daniewski, Ferdinan K. Lee, Keith A. Yagaloff It is certified that error appears in the above-indentified patent and that said Letters Patent is hereby corrected as shown below:

(3-phenyl-2-propenyl)-2-naphthalenyl]oxy]hexyl] benzenepropanoic Acid.--.

Signed and Sealed this

Twentieth Day of February, 1996

Attest:

BRUCE LEHMAN

Attesting Officer

Commissioner of Patents and Trademarks